United States Patent
Carmosin et al.

Patent Number: 5,565,456
Date of Patent: Oct. 15, 1996

[54] ANXIOLYTIC AROYL PIPERIDINYL AND PIPERAZINYLACYL PYRROLES

[75] Inventors: Richard J. Carmosin, Quakertown; John R. Carson, Norristown; Philip Pitis, North Wales, all of Pa.

[73] Assignee: Ortho Pharmaceutical Corporation, Raritan, N.J.

[21] Appl. No.: 403,966

[22] Filed: Mar. 15, 1995

Related U.S. Application Data

[62] Division of Ser. No. 172,696, Dec. 23, 1993, Pat. No. 5,418,236.

[51] Int. Cl.$^6$ ............... C07D 401/06; C07D 401/14; A61K 31/445; A61K 31/505
[52] U.S. Cl. .......... 514/252; 514/256; 514/318; 514/326; 544/333; 544/405; 546/194; 546/208
[58] Field of Search ................. 546/194, 208; 544/333, 405; 514/252, 256, 318, 326

[56] References Cited

U.S. PATENT DOCUMENTS

| | | | |
|---|---|---|---|
| 3,407,199 | 10/1968 | Pachter | 544/141 |
| 3,998,844 | 12/1976 | Carson | 548/539 |
| 5,332,736 | 6/1994 | Carmosin et al. | 514/235.5 |
| 5,418,236 | 5/1995 | Carmosin et al. | 514/252 |

*Primary Examiner*—Emily Bernhardt
*Attorney, Agent, or Firm*—John W. Harbour

[57] ABSTRACT

Aroyl(piperidinyl and piperazinyl)acyl pyrroles of the following formula have anxiolytic activity:

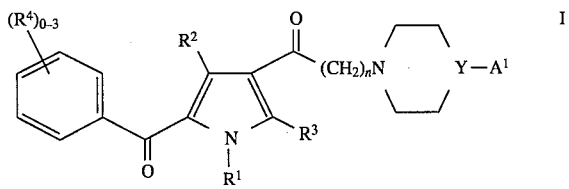

wherein,

Y is selected from the group consisting of N, CH or COH;
$A^1$ is selected from the group consisting of

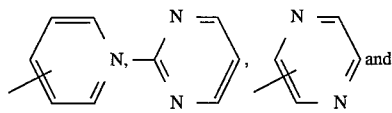 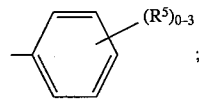

n is an integer from 1 to 5;
R1 is selected from the group consisting of H and $C_{1-4}$alkyl;
$R^2$ and $R^3$ are selected from the group consisting of H and $C_{1-4}$alkyl;
$R^4$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl; and
$R^5$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl; and acid addition salts thereof.

8 Claims, No Drawings

ANXIOLYTIC AROYL PIPERIDINYL AND PIPERAZINYLACYL PYRROLES

This is a division of application Ser. No. 08/172,696 filed Dec. 23, 1993, now U.S. Pat. No. 5,418,236, which is hereby incorporated by reference.

This invention relates to anxiolytics. More particularly, this invention relates to aroyl piperidinyl and piperazinylacyl pyrroles having anti-anxiety activity.

BACKGROUND OF THE INVENTION

Buspirone represents a new initiative in the treatment of anxiety. Conventional benzodiazepine anti-anxiety drugs, such as diazepam, cause

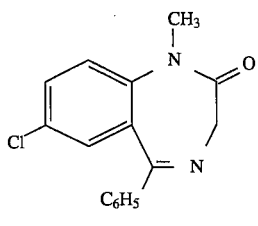

diazepam

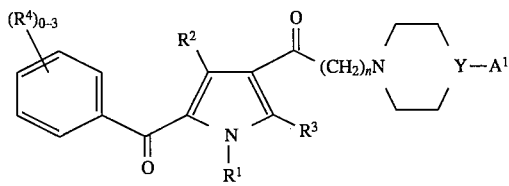

Buspirone physical dependence and sedation and interact with alcohol. Buspirone appears to lack these side effects. Buspirone, however, is not as efficacious as the benzodiazepines in patients who have had previous benzodiazepine therapy.

Buspirone is a partial agonist at the $5HT_{1A}$ receptor, and this is thought to be the mechanism of its anti-anxiety activity, as disclosed by New, J. S., "The discovery and development of buspirone: A new approach to the treatment of anxiety", *Med. Res. Rev.*, 10, 283–286 (1990). Buspirone was initially investigated as an anti-psychotic drug and binds to the $D_2$ receptor. Thus, while buspirone offers important advantages as an anti-anxiety agent, a compound with greater receptor specificity and greater affinity for the $5HT_{1A}$ receptor is desirable. Specifically, compounds which are anxiolytics and which are ligands at the $5HT_{1A}$ receptor should have improved selectivity for the $5HT_{1A}$ receptor versus the $5HT_2$, $D_2$ and $\alpha_1$ receptors.

SUMMARY OF THE INVENTION

Briefly, there are provided by the present invention compounds having anxiolytic activity of the formula:

![Formula I]

wherein,

Y is selected from the group consisting of N, CH or COH;

$A^1$ is selected from the group consisting of

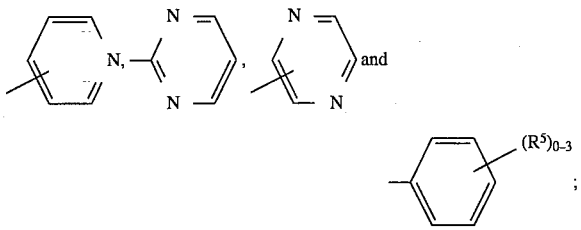

n is an integer from 1 to 5;

$R^1$ is selected from the group consisting of H and $C_{1-4}$alkyl;

$R^2$ and $R^3$ are selected from the group consisting of H and $C_{1-4}$alkyl;

$R^4$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl; and $R^5$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl; and acid addition salts thereof.

DETAILED DESCRIPTION OF THE INVENTION

Scheme 1 exemplifies the preparation of compounds of formula (I). Referring to Scheme 1, in the first step a simple pyrrole A1 is acylated with an appropriately substituted benzoyl chloride B1 to produce benzoyl pyrrole C1. This acylation may be carried out by simply heating the benzoyl chloride and the pyrrole in an aprotic solvent followed by removing excess benzoyl chloride by reaction with a dibasic amine and extraction with HCl. Typical of the aprotic solvents which may be utilized are aromatic hydrocarbons, such as, benzene, toluene, xylene, chlorobenzene, nitrobenzene, etc.; paraffins, such as, methyl cyclohexane, octane, etc.; halocarbons, such as, methylene chloride, chloroform, tetrachloroethane, etc.; ethers, such as, diethyl ether, diglyme, etc.; ketones, such as, methyl ethyl ketone, cyclohexanone, etc.; esters, such as, ethyl butyrate, etc.; nitroalkanes, such as, nitropropane, etc.; or carbon disulfide. The temperature of the acylation will vary depending upon the desired rate of reaction and the substituents of pyrrole A1. Preferably the acylation is carried out at a temperature of from 50° to 250° C. A suitable dibasic amine is dimethyl-3-aminopropyl amine. In the case where $R^1$ is hydrogen the acylation, as described, may not produce desirable yields. In this case, a Vilsmeier type acylation as employed by J. White and G. McGillivrey, J. Org. Chem., Vol. 42, pp 42–48, 1977 might be expeditiously employed.

Subsequently, benzoyl pyrrole C1 is acylated at the 4-position in a Friedel-Crafts reaction with acid chloride D1 to produce 2-benzoyl-4-alkanoyl pyrrole E1. The Friedel-Crafts reaction is carried out by causing the carboxylic acid chloride D1, in which X is Cl, Br or I, to react with product C1 in a solvent with a Friedel-Crafts catalyst(s) followed by treatment with HCl and evaporation of the solvent. Suitable Friedel-Crafts catalyst(s) include aluminum chloride, zinc chloride, $BF_3$ or $TiCl_4$. Suitable solvents include methylene chloride, 1,2-dichloroethane, carbon tetrachloride or chloroform. The reaction temperature might vary between −20° and 150° C. In the case where $R^4$ is amine, it will not survive the Friedel-Crafts reaction in good yield. Thus, it should be protected with well known protecting groups or present as a suitable precursor substituent, such as, nitro which can thereafter be converted to amine. In the third reaction, 2-benzoyl-4-alkanoyl pyrrole E1 is aminated with amine F1 to produce the desired 2-benzoyl-4-aminoalkanoyl pyrrole G1. The amination may be carried out by heating the reactants E1 and F1 neat or in a solvent to a temperature of from 40° to 120° C. and preferably from 50° to 90° C. Suitable solvents, where employed, include ethanol, i-propanol or toluene.

SCHEME 1

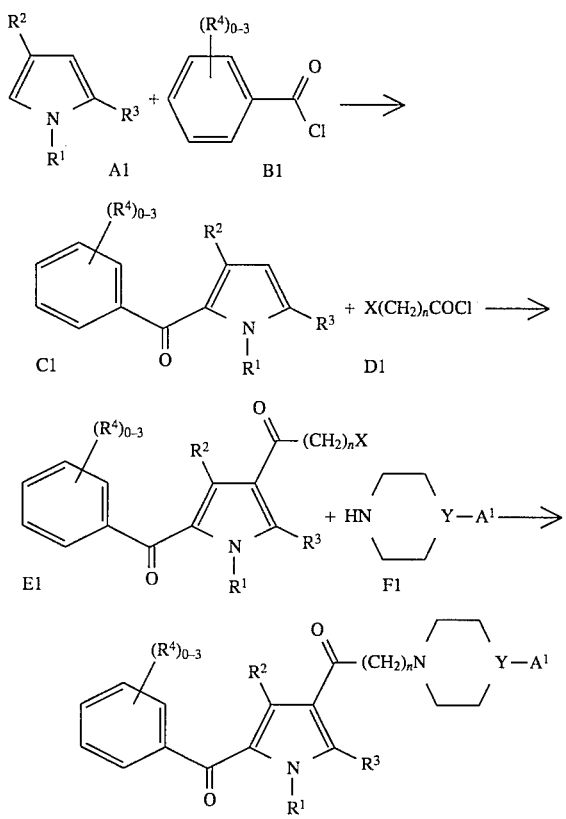

Preferred $R^1$ include hydrogen, methyl, ethyl, n-propyl and i-propyl. In the most preferred compounds, $R^1$ is methyl.

Preferred $R^2$ and $R^3$ include hydrogen, methyl, ethyl, n-propyl and i-propyl. In the most preferred compounds, $R^2$ and $R^3$ are hydrogen and methyl.

Preferred $R^6$ include bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl, and acetyl. In the most preferred compounds, $R^6$ is non-existant, methly or chloro.

The compounds herein readily form pharmaceutically acceptable acid addition salts. Such salts include hydrochlorides, sulfates, phosphates, methanesulfonates, fumarates, maleates, citrates, lactates, and the like. Those skilled in the art will readily recognize suitable methods for manufacture and use of the acid addition salts.

The compounds of formula (1) are useful as antianxiety agents by virtue of their ability to bind to the 5-$HT_1A$ receptor. The test compounds were assayed as follows:

5-$HT_{1A}$ assay

The 5-$HT_{1A}$ assay used a $P_2$ fraction (synaptosomal membranes) from the cerebral cortex of male, Wistar rats. The ligand $3_{H-8}$-hydroxy-DPAT was used in competitive binding experiments at a concentration of 3 nM, and 1 mM serotonin as a blank determinant. Incubation was in 3 mM potassium phosphate buffer for 20 min at 25° C. Under these conditions, specific binding constituted 85% of total binding, and the $K_i$ values for some known drugs were: 0.32 nM for WB4101, 59 nM for phentolamine, and 111 nM for clozapine.

The data from each assay were analyzed by calculating the percent inhibition of the binding of the tritiated ligands by given concentrations of the test compound. $K_i$ values, where given, were obtained from the logit analysis of concentration-inhibition curves.

Binding of compounds of this invention to the $5HT_{1A}$ is shown in Table 1:

TABLE 1

| Example Compound | % Inhibition at 1 μm or $K_i$ |
|---|---|
| 5 | $K_i$ 7.7 nM |
| 6-1 | 24% |
| 6-2 | 94% |
| 6-3 | 83% |
| 6-4 | 91% |
| 6-5 | 67% |
| 6-6 | $K_i$ 6.0 nM |
| 7 | $K_i$ 15 nM |
| 8 | 69% |

The compounds from examples 5 and 7 showed no inhibition in binding to the $D_2$, 5-$HT_2$ or $\alpha_1$ receptors at 1 μM, thus exhibiting excellent selectivity. By comparison, buspirone showed $K_i$ (nM) values of 5.7 (5$HT_{1A}$), 362 ($D_2$), 174 (5-$HT_2$) and 138 ($\alpha_1$).

The anxiolytic activity of selected compounds of the invention was assessed by determining their ability to release (disinhibit) behavior that had been suppressed by punishment (Vogel, J. R. et al. Psychopharmacology 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase (p<0.05, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there was a significant difference in the median number of shocks tolerated between the drug-treated group and the control group.

At a dose of 5 mg/kg IP, the compound of Example 5 caused a 240% change in responding while at a dose of 10 mg/kg IP, the compound of Example 7 caused a 180% change in responding.

To prepare the pharmaceutical compositions of this invention, one or more compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The following examples are offered by way of illustration and not by way of limitation.

EXAMPLE 1

(1-Methyl-1H-pyrrol-2-yl)(4-nitrophenyl)-methanone (1).

A solution of 70 g (0.86 mole) N-methylpyrrole and 206 g (1.11 mole) of p-nitrobenzoyl chloride in 850 mL of dry toluene was heated under reflux with an argon stream bubbling through for 18 h. The reaction was cooled and 560 mL of 20% N,N-dimethylaminopropylamine was added and stirred for 2 h. $Et_2O$ was added, the solid was filtered and the filtrate was washed with $H_2O$, 1N HCl, twice with sodium bicarbonate, $H_2O$, brine, and dried ($MgSO_4$). The solvent was removed in vacuo. Recrystallization from $CH_2Cl_2$/MeOH gave 145.45 g of solid (73%). mp.148°–150° C. mass spectrum (Cl-$CH_4$) m/z 231 (M+ 1). NMR (CDCl$_3$) δ8.3 (d, 2 H); 7.9 (d, 2 H); 7.0 (m, 1 H); 6.7 (m, 1 H); 6.2 (m, 1 H); 4.05 (s, 3 H). Anal calcd for $C_{12}H_{10}N_2O_3 \cdot 0.16 H_2O$: C, 61.83, H, 4.47, N, 12.02, $H_2O$, 0.77. Found: C, 62.04, H, 4.46, N, 12.03, $H_2O$, 0.81.

EXAMPLE 2

Using the procedure of Example 1 and employing the appropriate aroyl chloride in place of p-nitrobenzoyl chloride, the following products were obtained:

(2-Chlorophenyl)(1-methyl-1H-pyrrol-2-yl)-methanone (2-1): mp 55°–57 ° C. Anal calcd for $C_{12}H_{10}ClN_2O_3$: C, 70.93; H, 4.96; N, 6.89 Found: C, 70.91; H, 4.89; N, 6.88

(4-Fluorophenyl)(1-methyl-1H-pyrrol-2-yl)-methanone (2-2): mp 48°–50 ° C. Anal calcd for $C_{12}H_{10}FN_2O_3$: C, 65.61, H, 4.59, N, 6.30 Found: C, 65.48, H, 4.42, N, 6.32

EXAMPLE 3

2-Chloro-1-[5-(4-nitrobenzoyl)-1-methyl- 1H-pyrrol-3-yl]-ethanone (3), A 210 g (1.57 mole) sample of $AlCl_3$ was added in portions to a solution of 145.4 g (0.63 mole) of (1-methyl-1H-pyrrol-2-yl)(4-nitrophenyl)-methanone (1) in 450 mL of 1,2-dichloroethane (DCE). A solution of 125 mL (1.57 mole) of chloroacetyl chloride in 200 mL of DCE was added dropwise. The mixture was stirred 1 h at room temperature. The reaction was poured into 1N HCl and ice, the organics were separated, washed with $H_2O$, 1N NaOH, $H_2O$, brine and dried ($MgSO_4$). The solvent was evaporated in vacuo and the residue was recrystallized from EtOAc/EtOH to give 116.2 g of solid. mp 173°–176° C. Mass spectrum (Cl-$CH_4$) m/z 307 (M+1). NMR ($Me_2SO$-$d_6$) 8.4 (d, 2 H); 8.2 (s,1 H); 8.0 (d, 2 H); 7.1 (s, 1 H); 4.8 (s, 2 H); 4.0 (s, 3 H). Anal calcd for $C_{14}H_{11}ClN_2O_4$: Calcd: C, 54.83; H, 3.61; N, 9.13. Found: C, 55.11; H, 3.70; N, 9.10.

EXAMPLE 4

Using the procedure of Example 3 and employing the appropriate aryl pyrroyl methanone, from Example 2 or known to the art, in place of (1-methyl-1H-pyrrol-2-yl)(4-nitrophenyl)-methanone and the appropriate ψ-chloroacyl chloride in place of chloroacetyl chloride, the following products (4-1 through 4-5) were obtained:

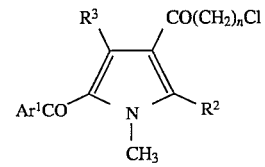

| No. | Ar$^1$ | R$^2$/R$^3$ | n |
|---|---|---|---|
| 4-1 | o-ClPh | H/H | 1 |
| 4-2 | p-ClPh | H/H | 1 |
| 4-3 | p-ClPh | CH$_3$/CH$_3$ | 1 |
| 4-4 | p-ClPh | CH$_3$/CH$_3$ | 4 |
| 4-5 | p-FPh | H/H | 1 |

They are described as follows:

| No. | M.P. °C. | Formula | Calc'd/ Found |
|---|---|---|---|
| 4-1 | 121–124 | $C_{14}H_{11}Cl_2NO_2$ | C, 56.78; H, 3.74; N, 4.73 |
|     |         |                         | C, 56.72; H, 3.66; N, 4.70 |
| 4-2 | 163     | $C_{14}H_{11}Cl_2NO_2$ | C, 56.78; H, 3.74; N, 4.73 |
|     |         |                         | C, 56.63; H, 3.82; N, 4.63 |
| 4-3 | 141–143 | $C_{16}H_{15}Cl_2NO_2$ | C, 59.28; H, 4.66; N, 4.32 |
|     |         |                         | C, 59.32; H, 4.73; N, 4.33 |
| 4-4 | 60–65   | $C_{19}H_{21}Cl_2NO_2$ | C, 62.30; H, 5.78; N, 3.82 |

| No. | M.P. °C. | Formula | Calc'd/ Found |
|---|---|---|---|
| 4-5 | 149–151 | C₁₄H₁₁FClNO₂ | C, 62.35; H, 5.74; N, 3.75<br>C, 60.12; H, 3.96; N, 5.01<br>C, 60.31; H, 3.91; N, 4.88 |

EXAMPLE 5

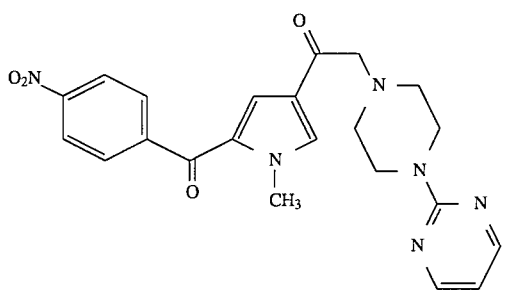

1-[1-Methyl-5-(4-nitrobenzoyl)-1H-pyrrol- 3-yl]-2-[4-(2-pyrimidinyl)-1-piperazinyl]ethanone (5).

A solution of 5.4 g (0.013 mole) of 1-(2-pyrimidinyl)-piperazine in 20 mL of 2-PrOH was added dropwise to a solution of 4.0 g (0.013 mole) of 2-chloro-1-[5-(4-nitrobenzoyl)-1-methyl-1H-pyrrol-3-yl]ethanone (3) in 30 mL of 2-PrOH under reflux. After 2 h, the solid was filtered and the filtrate cooled in a ice bath. The precipitate was collected and combined with the first solid. The solid was dissolved in Et₂O and THF, washed with H₂O, brine, and dried (MgSO₄). The solvent was evaporated in vacuo. The residue was recrystallized from EtOH then again from EtOH/2-PrOH to give 2.96 g (52%). mp.164°–166° C. Mass spectrum (Cl-CH₄) m/z 435 (M+1). NMR (CDCl₃) δ8.35 (m,4 H); 7.95 (d, 2 H) ;7.8 (s, 1 H); 7.2 (s, 1 H); 6.5 (m, 1 H); 4.1 (s, 3 H); 3.9 (m, 4 H); 3.55 (s, 2 H); 2.6 (m, 4 H). Anal calcd for C₂₂H₂₂N₆O₄ C, 60.82; H, 5.10; N, 19.34. Found: C, 60.92; H, 5.14; N, 19.11.

EXAMPLE 6

Using the procedure of Example 5 and employing the appropriate 1-( 5-aroylpyrrol-3-yl)-ψ-chloroalkanone, from Example 4, in place of 2-chloro-1-[5-(4-nitrobenzoyl)-1-methyl- 1H-pyrrol-3-yl]ethanone and the appropriate N-arylpiperazine in place of 1-(2-pyrimidinyl)piperazine, the following products (6-1 through 6-6) were obtained:

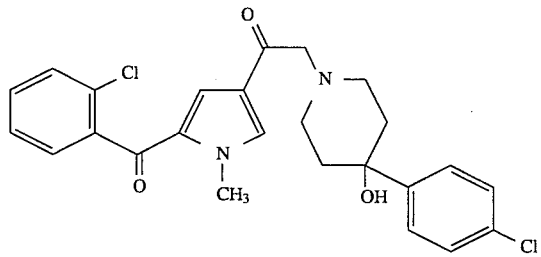

| No. | Ar¹ | Ar² | R²/R³ | n |
|---|---|---|---|---|
| 6-1 | p-ClPh | 2-Pyrimidinyl | CH₃/CH₃ | 1 |
| 6-2 | p-ClPh | 2-Pyridinyl | H/H | 1 |
| 6-3 | o-ClPh | 2-(2-Propoxy)phenyl | H/H | 1 |
| 6-4 | p-FPh | 2-Pyrimidinyl | H/H | 1 |
| 6-5 | p-ClPh | 1-Naphthyl | H/H | 1 |
| 6-6 | p-ClPh | 2-Pyrimidinyl | CH₃/CH₃ | 4 |

They are described as follows:

| No. | M.P. °C. | Formula | calc'd/ found |
|---|---|---|---|
| 6-1 | 122–124 | C₂₄H₂₆ClN₅O₂ | C, 63.78; H, 5.80; N, 15.50<br>C, 63.79; H, 5.71; N, 15.48 |
| 6-2 | 133–135 | C₂₃H₂₃ClN₄O₂ | C, 65.32; H, 5.48; N, 13.25<br>C, 65.35; H, 5.36; N, 13.21 |
| 6-3 | 230–233 | C₂₇H₃₀ClN₃O₃/ HCl | C, 62.79; H, 6.05; N, 8.14<br>C, 62.78; H, 6.09; N, 7.98 |
| 6-4 | 240–241 | C₂₂H₂₂FN₅O₂/ 1.75 HCl/1.5 H₂O | C, 53.03; H, 5.41; N, 14.05; Cl, 12.45; H₂O, 5.42<br>C, 53.09; H, 5.55; N, 13.96; Cl, 12.83; H₂O, 5.52 |
| 6-5 | 178–180 | C₂₈H₂₆ClN₃O | C, 71.25; H, 5.55; N, 8.96<br>C, 71.40; H, 5.64; N, 8.69 |
| 6-6 | 214–215 | C₂₇H₃₂ClN₅O₂/ 2 HCl | C, 57.20; H6.04; N, 12.35<br>C, 56.89; H, 6.14; N, 12.30 |

EXAMPLE 7

1-[5-(2-Chlorobenzoyl)-1-methyl-1H-pyrrol- 3-yl]-2-[4-(4-chlorophenyl)- 4-hydroxy-1-piperidinyl]ethanone Hydrochloride(7).

A solution of 4.3 g (0.022 mole) of 4-(4'-chlorophenyl)-4-hydroxypiperidine and 3 mL of diisopropylethylamine in 10 mL of 2-PrOH was added in portions to a solution of 5 g (0.017 mole) of 2-chloro-1-[5-(2-chlorobenzoyl)- 1-methyl-1H-pyrrol-3-yl]ethanone (4-1) in 15 mL of 2-PrOH. The mixture was heated under reflux for one hour, cooled and the solvent was evaporated in vacuo. The residue was partitioned between a mixture of THF/Et₂O and H₂O. The organics were extracted three times with 1 N HCl, the aqueous layer was made basic with NaHCO₃, and extracted with a THF/Et₂O mixture. The organics were washed with H₂O, brine and dried (MgSO₄). The solvent was evaporated in vacuo. The residue was converted to the hydrochloride salt with ethereal HCl and 2-PrOH. The solid was recystallized from EtOH/2-PrOH to give 5.51 g (64%) of product. mp. 170° C. Mass spectrum (Cl-CH₄) m/z 472 (M+1). NMR (Me₂SO_d₆) δ8.2 (s, 1 H); 7.4-7.6 (m, 8 H); 6.9 (s, 1 H); 5.65 (bs, 1 H); 4.8 (bs, 1 H); 4.1 (s, 3 H); 2.4 (m, 2 H); 1.8 (m, 2 H). Anal calcd for C₂₅H₂₄Cl₂N₂O₃.HCl.C₂H₅O: C, 58.55; H, 5.64; N, 5.06. Found: C, 58.59; H, 5.53; N, 5.14.

EXAMPLE 8

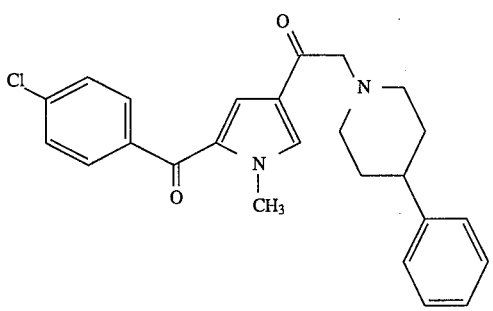

Using the procedure of Example 7 and employing 2-chloro-1-[5-(4-chlorobenzoyl)-1-methyl-1H-pyrrol-3-yl]-ethanone (4-2) in place of 2-chloro- 1-[5-(2-chlorobenzoyl)-1-methyl-1H-pyrrol-3-yl]ethanone and 4-phenylpiperidine in place of 4-(4'-chlorophenyl)-4-hydroxypiperidine, 1-[5-( 4-chlorobenzoyl)-1-methyl-1H-pyrrol-3-yl]-2-(4-phenylpiperidinyl)-ethanone (8) was obtained: mp 123°–125° C. Anal calcd for $C_{25}H_{25}ClN_2O_3$: C, 62.41; H, 5.53; N, 8.09. Found: C, 62.44; H, 5.91; N, 8.05.

What is claimed is:

1. A compound having anxiolytic activity of the formula:

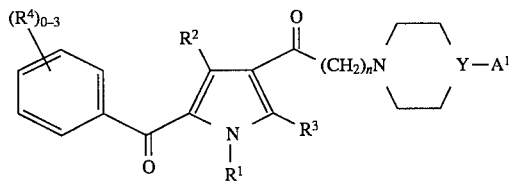

wherein,

Y is selected from the group consisting of CH or COH;
$A^1$ is selected from the group consisting of

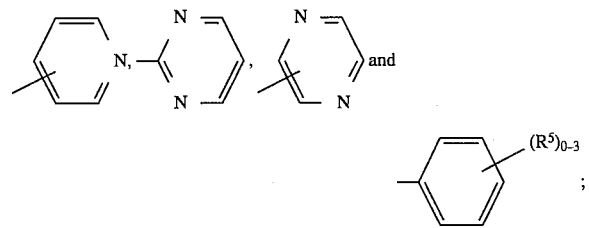

n is an integer from 1 to 5;
$R^1$ is selected from the group consisting of H and $C_{1-4}$alkyl;
$R^2$ and $R^3$ are selected from the group consisting of H and $C_{1-4}$alkyl;
$R^4$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl; $C_{1-4}$alkylsulfonyl, $C_{1-4}$alkylsulfinyl and $C_{1-4}$acyl; and
$R^5$ is selected from the group consisting of halo, $C_{1-4}$alkyl, hydroxy, $C_{1-4}$ alkoxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl; or pharmaceutically acceptable acid addition salts thereof.

2. The compound of claim 1 wherein $R^1$ is selected from the group consisting of hydrogen, methyl, ethyl, n-propyl and i-propyl.

3. The compound of claim 1 wherein $R^2$ and $R^3$ are independently selected from the group consisting of hydrogen, methyl, ethyl, n-propyl and i-propyl.

4. The compound of claim 1 wherein $R^4$ is absent or selected from the group consisting of bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl, and acetyl.

5. The compound of claim 1 which is a pharmaceutically acceptable acid addition salt selected from the group consisting of hydrochlorides, sulfates, phosphates, methanesulfonates, fumarates, maleates, citrates and lactates.

6. A compound selected from the group consisting of:

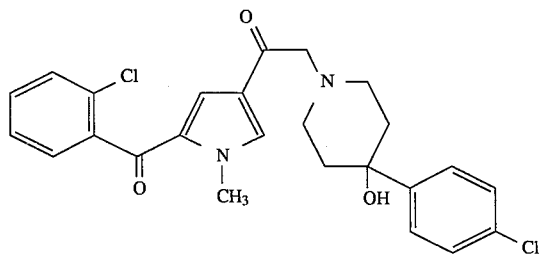

and

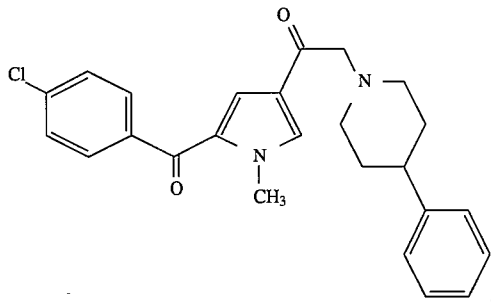

7. A pharmaceutical composition effective as an anxiolytic in mammals comprising a pharmaceutically acceptable carrier and an effective amount of the compound of claim 1.

8. A method for inducing an anxiolytic effect in mammals comprising the step of administering an effective amount of the compound of claim 1 in admixture with a pharmaceutically acceptable carrier.

* * * * *